United States Patent
Sadik

(10) Patent No.: US 12,161,109 B2
(45) Date of Patent: Dec. 10, 2024

(54) PACKAGING FOR WET TISSUE STORAGE

(71) Applicant: Axogen Corporation, Alachua, FL (US)

(72) Inventor: Mindy E. Sadik, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 594 days.

(21) Appl. No.: 17/504,668

(22) Filed: Oct. 19, 2021

(65) Prior Publication Data

US 2022/0125044 A1 Apr. 28, 2022

Related U.S. Application Data

(60) Provisional application No. 63/104,411, filed on Oct. 22, 2020.

(51) Int. Cl.
*A01N 1/02* (2006.01)

(52) U.S. Cl.
CPC ......... *A01N 1/0242* (2013.01); *A01N 1/0278* (2013.01)

(58) Field of Classification Search
CPC .................................................. A01N 1/0242
See application file for complete search history.

(56) References Cited

U.S. PATENT DOCUMENTS

| | | | |
|---|---|---|---|
| 4,012,288 A * | 3/1977 | Lyman | C12M 23/12 435/305.2 |
| 4,838,288 A | 6/1989 | Wright et al. | |
| 5,795,775 A * | 8/1998 | Lahm | B01L 3/508 435/297.5 |
| 10,806,558 B1 | 10/2020 | Perry | |
| 2002/0029981 A1 | 3/2002 | Nigam | |
| 2003/0168370 A1 | 9/2003 | Merboth et al. | |
| 2013/0277261 A1 | 10/2013 | Kinyon | |
| 2013/0325111 A1 | 12/2013 | Campbell et al. | |
| 2017/0164606 A1 | 6/2017 | Suzuki et al. | |
| 2018/0193127 A1 | 7/2018 | Poyss et al. | |
| 2020/0390087 A1 | 12/2020 | Sadik | |
| 2020/0390088 A1 | 12/2020 | Sadik | |

FOREIGN PATENT DOCUMENTS

| | | |
|---|---|---|
| WO | 00/54584 A1 | 9/2000 |
| WO | 01/93784 A2 | 12/2001 |

OTHER PUBLICATIONS

International Search Report and Written Opinion issued in International Application No. PCT/US2021/055711, issued Apr. 5, 2022 (22 pages).

International Search Report and Written Opinion issued in International Application No. PCT/US2021/055713, issued Apr. 11, 2022 (20 pages).

Packaging World: "Artegraft switches to copolyester for vascular graft tubes", Jan. 10, 2008, pp. 1-3, XP055886433.

* cited by examiner

*Primary Examiner* — Rosanne Kosson
(74) *Attorney, Agent, or Firm* — Bookoff McAndrews PLLC

(57) ABSTRACT

A packaging system is provided. The packaging system may include a packaging body defining a cavity. The packaging system may also include a tissue cradle configured to be disposed within the cavity. The packaging system may also include a seal configured to be joined to the packaging body to fluidly seal the cavity. Such packaging systems may be used in the storage of wet-preserved or dry-preserved human or animal tissue. Also provided are a packaged tissue specimen and a method for packaging tissue.

25 Claims, 5 Drawing Sheets

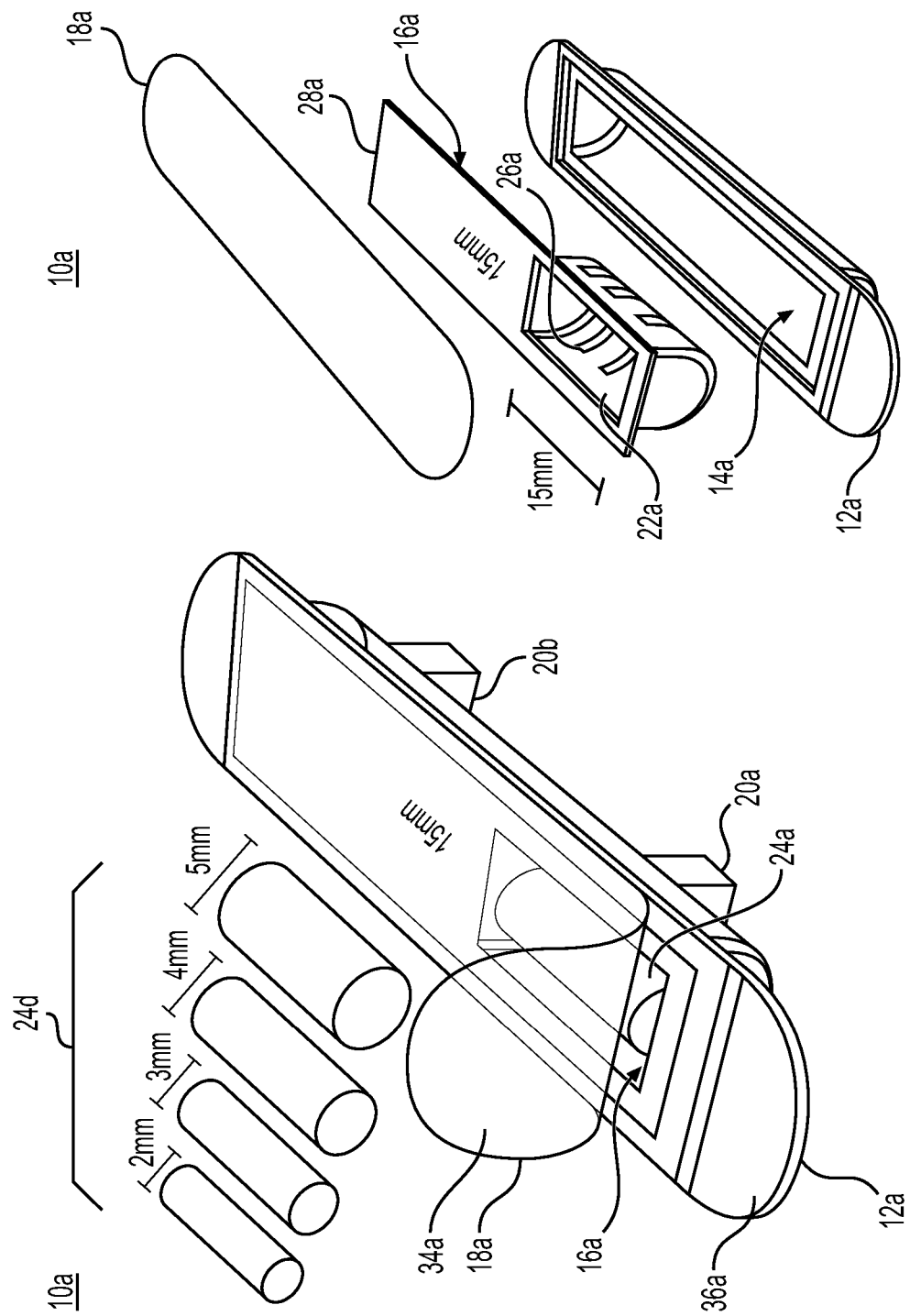

PACKAGING FOR WET TISSUE STORAGE

CROSS-REFERENCE TO RELATED APPLICATIONS

This patent application claims the benefit under 35 U.S.C. § 120 to U.S. Provisional Patent Application No. 63/104,411, filed on Oct. 22, 2020, the entirety of which is incorporated herein by reference.

TECHNICAL FIELD

The present disclosure generally relates to a packaging system for tissue specimens, and more particularly to packaging arrangements for the storage of tissue in a liquid medium.

BACKGROUND

Biological tissues may often provide improved functional performance as compared to equivalent synthetic devices when used in in vivo implantation. However, the availability and usage of tissue grafts may be restricted by inherent supply constraints and logistic concerns of harvest, transportation and storage. Various techniques have been developed that allow for the harvesting, delivery, and storage of tissues that may be suitable for use in surgical implantation. However, many of the developed techniques may require the use of specialized refrigeration equipment for storing the donor tissue at extremely low temperature. Such requirements may frequently restrict the facilities that are able to make use of the available tissues, and may complicate the transportation of tissue to end-use surgical facilities. The packaging and related methods described herein overcome some of these issues and may enable a more convenient approach to the transport, storage, pre-operative preparation and ultimate use of wet-preserved or dry-preserved tissue. In some suitable storage approaches, the tissue may be stored in a preservative solution that may prolong the useful storage life of the tissue. In some such storage approaches, the tissue may be retained in the preservation solution until the tissue is used in a surgical setting.

SUMMARY

According to an implementation, a packaging system may include a packaging body defining a cavity. The packaging system may also include a tissue cradle configured to be disposed within the cavity. The packaging system may further include a seal configured to be joined to the packaging body to fluidly seal the cavity.

One or more of the following features may be included. The cavity may be configured to receive tissue cradles of different sizes. The cavity may include at least one slot configured to engage a corresponding tab of the tissue cradle for maintaining a position of the tissue cradle within the cavity.

The tissue cradle may be configured to support a tissue specimen. The tissue cradle may be configured to at least partially immerse the tissue specimen in a liquid disposed in the cavity. The tissue cradle may be configured to allow the liquid to drain from the tissue cradle upon removal from the cavity. The tissue cradle may include one or more openings to allow the liquid to drain from the tissue cradle upon removal from the cavity.

The tissue cradle may include one or more features configured to facilitate manipulation of the tissue cradle. The tissue cradle may be configured to support tissue specimens having a plurality of sizes. The tissue cradle may include one of a plurality of tissue cradles. Each of the plurality of tissue cradles may be configured to support differently-sized tissue specimens. The cavity and each of the plurality of tissue cradles may include cooperating features to support any of the plurality of tissue cradles within the cavity.

The seal may include a plastic film. The seal may include a foil seal. The seal may be configured to be peeled from the packaging body to allow access to the cavity.

According to another implementation, a packaged tissue specimen is provided, wherein a tissue specimen is packaged in a tissue packaging system. The tissue packaging system may include a packaging body defining a cavity. The tissue packaging system may also include a tissue cradle configured to be disposed within the cavity. The tissue packaging system may further include a seal configured to be joined to the packaging body to fluidly seal the cavity. The tissue specimen may be supported by the tissue cradle.

One or more of the following features may be included. The cavity may be configured to receive tissue cradles of different sizes. The tissue specimen may include one or more human tissue, including but not limited to, nerve tissue, vascular tissue, urological tissue, skin tissue, tendons, and muscle tissue. The tissue specimen may include one or more animal tissue, including but not limited to nerve tissue, vascular tissue, urological tissue, skin tissue, tendons, and muscle tissue.

The tissue cradle may be configured to at least partially immerse the tissue specimen in a liquid disposed in the cavity. The tissue cradle may be configured to allow the liquid to drain from the tissue cradle upon removal from the cavity. The tissue cradle may include one or more openings to allow the liquid to drain from the tissue cradle upon removal from the cavity. The tissue cradle may include one or more features configured to facilitate manipulation of the tissue cradle. The tissue cradle may be configured to support tissue specimen having one of a plurality of sizes. The tissue cradle may include one of a plurality of tissue cradles. Each of the plurality of tissue cradles may be configured to support one of a plurality of tissue specimens of a different size. The cavity and each of the plurality of tissue cradles may include cooperating features to support any of the plurality of tissue cradles within the cavity.

The seal may include a plastic film. The seal may include a foil seal. The seal may be configured to be peeled from the packaging body to allow access to the cavity.

According to yet another implementation, a method of packaging tissue may include supporting a tissue specimen within a tissue support cradle. The method may include placing the tissue support cradle within a cavity defined in a packaging body. The method may include at least partially filling the cavity with a liquid. The method may also include coupling a seal to the packaging body to fluidly seal the cavity.

One or more of the following features may be included. The tissue cradle may be selected from a plurality of tissue cradles of different sizes. The cavity may be configured to receive each of the tissue cradles of different sizes. The tissue specimen may include one or more of nerve tissue, vascular tissue, urological tissue, tendons, and muscle tissue.

The tissue cradle may be configured to at least partially immerse the tissue specimen in the liquid disposed in the cavity. The tissue cradle may be configured to allow the liquid to drain from the tissue cradle upon removal from the cavity. The tissue cradle may include one or more openings to allow the liquid to drain from the tissue cradle upon removal from the cavity.

The tissue cradle may include one or more features configured to facilitate manipulation of the tissue cradle. The tissue cradle may be configured to support the tissue specimen selected from a plurality of tissue specimens of different sizes. The tissue cradle may include one of a plurality of tissue cradles. Each of the plurality of tissue cradles may be configured to support tissue specimens of a different size. The cavity and each of the plurality of tissue cradles may include cooperating features to support any of the plurality of tissue cradles within the cavity.

The seal may include one of a plastic seal and a foil seal. Coupling the seal to the packaging body may include one of adhesively bonding and heat sealing. The seal may be configured to be peeled from the packaging body to allow access to the cavity.

According to another implementation, a packaging system may include a packaging body defining a cavity and one or more reservoirs. The packaging system may further include a seal configured to be joined to the packaging body to fluidly seal the cavity and the one or more reservoirs.

One or more of the following features may be included. The cavity may be configured to support a tissue specimen. The packaging system may further include one or more tissue cradles configured to be disposed within the cavity. The one or more tissue cradles may be configured to support a tissue specimen. The seal may be configured to be incrementally peelable from the packaging body to incrementally allow access to the cavity and the one or more fluid reservoirs.

The packaging system may further include one or more fluid pathways between the cavity and the one or more reservoirs. The one or more fluid pathways may include a frangible seal configured to fluidly isolate the cavity and the one or more reservoirs in a sealed condition. The frangible seal may be configured to provide fluid communication between the cavity and the one or more reservoirs in a ruptured condition. The frangible seal may be configured to be ruptured when a fluid pressure within the one or more reservoirs is increased above a threshold pressure. The frangible seal may include a region of lesser bond strength between the seal and the packaging body along the one or more fluid pathways. The frangible seal may include a rupturable member disposed in the one or more fluid pathways.

The packaging system may further include a drain between the cavity and an exterior of the packaging system. The drain may include a frangible seal configured to fluidly isolate the cavity from the exterior of the packaging system via the drain in a sealed condition. The drain may include a frangible seal configured to fluidly couple the cavity with the exterior of the packaging system via the drain in a ruptured condition.

According to a further implementation, a packaged tissue specimen is provided, in which the tissue specimen is packaged in a tissue packaging system that may include a packaging body defining a cavity and one or more reservoirs. The packaging system may also include a seal joined to the packaging body to fluidly seal the cavity and the one or more reservoirs. The tissue specimen is disposed within the cavity.

One or more of the following features may be included. The packaging system may further include a tissue cradle disposed within the cavity. The tissue cradle may support the tissue specimen disposed within the cavity. The seal may be configured to be incrementally peelable from the packaging body to incrementally allow access to the cavity and the one or more fluid reservoirs.

One or more fluid pathways may be provided between the cavity and the one or more reservoirs. The one or more fluid pathways may include a frangible seal configured to fluidly isolate the cavity and the one or more reservoirs in a sealed condition. The frangible seal may be configured to provide fluid communication between the cavity and the one or more reservoirs in a ruptured condition. The frangible seal may be configured to be ruptured when a fluid pressure within the one or more reservoirs is increased above a threshold pressure. The frangible seal may include a region of lesser bond strength between the seal and the packaging body along the one or more fluid pathways. The frangible seal may include a rupturable member disposed in the one or more fluid pathways.

The packaging system may also include a drain between the cavity and an exterior of the packaging system. The drain may include a frangible seal configured to fluidly isolate the cavity from the exterior of the packaging system via the drain in a sealed condition. The drain may include a frangible seal configured to fluidly couple the cavity with the exterior of the packaging system via the drain in a ruptured condition.

The tissue specimen may be at least partially disposed in a liquid. The one or more reservoirs may include a wash solution. The wash solution may be configured to be at least partially transferred to the cavity via the one or more fluid pathways.

BRIEF DESCRIPTION OF THE DRAWINGS

FIG. 1A depicts a first example embodiment of a packaging system consistent with the present disclosure;

FIG. 1B is an exploded view of the example embodiment of the packaging system of FIG. 1A, consistent with the present disclosure;

DETAILED DESCRIPTION OF EXAMPLE EMBODIMENTS

Figure 2A:
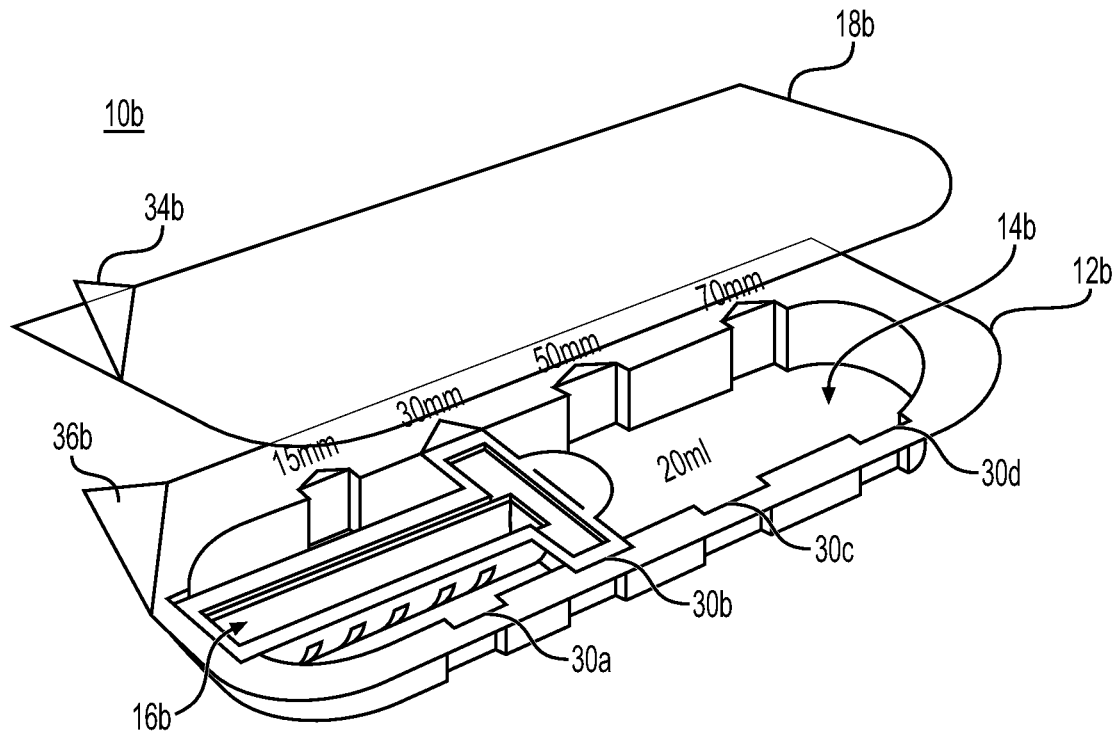
FIG. 2A depicts a second example embodiment of a packaging system consistent with the present disclosure.

In general, embodiments consistent with the present disclosure may relate to packaging systems. In some implementations, the packaging systems may be utilized for packaging tissue specimen, for example, which may be intended for use in connection with various surgical procedures, such as for grafts or other uses. In some example embodiments, the packaging systems may allow tissue specimens to be packaged in a liquid medium, e.g., which may facilitate storage or preservation of the tissue. In some embodiments, the liquid may include a preservation liquid and/or solution. Further, in some example embodiments, the packaging systems consistent with the present disclose may include features that may make it easier to manipulate the tissue specimens, for example when removing the tissue specimen from the packaging and/or during other operations.

For example, and referring to FIGS. 1A and 1B, an example packaging system 10a is generally shown. Consistent with the example embodiment, the packaging system 10a may generally have a blister packing configuration, including a packaging body 12a defining a cavity 14a. A tissue cradle 16a may be configured to be disposed within the cavity 14a, and the packaging system may further include a seal 18a that is configured to be joined to the packing body 12a to fluidly seal the cavity 14a.

Consistent with the present disclosure, the packaging body 12a may be formed from any suitable material, including but not limited to various plastic materials. In some embodiments, the packaging body 12a may be formed from a plastic material that permits sterilization, such as through gamma sterilization, or other suitable sterilization technique that may allow the packaging system 10a and/or anything contained within the packaging system 10a to be sterilized. In some embodiments, the packaging body 12a may be formed from a suitable material that may provide an oxygen barrier, e.g., to prevent oxygen from migrating into the interior of the cavity 14a. In some embodiments, the packaging body 12a may be formed from a multi-layer plastic material. The packaging body 12a may be formed by way of any suitable forming techniques, including, but not limited to, thermoforming or injection molding.

Figure 3A:
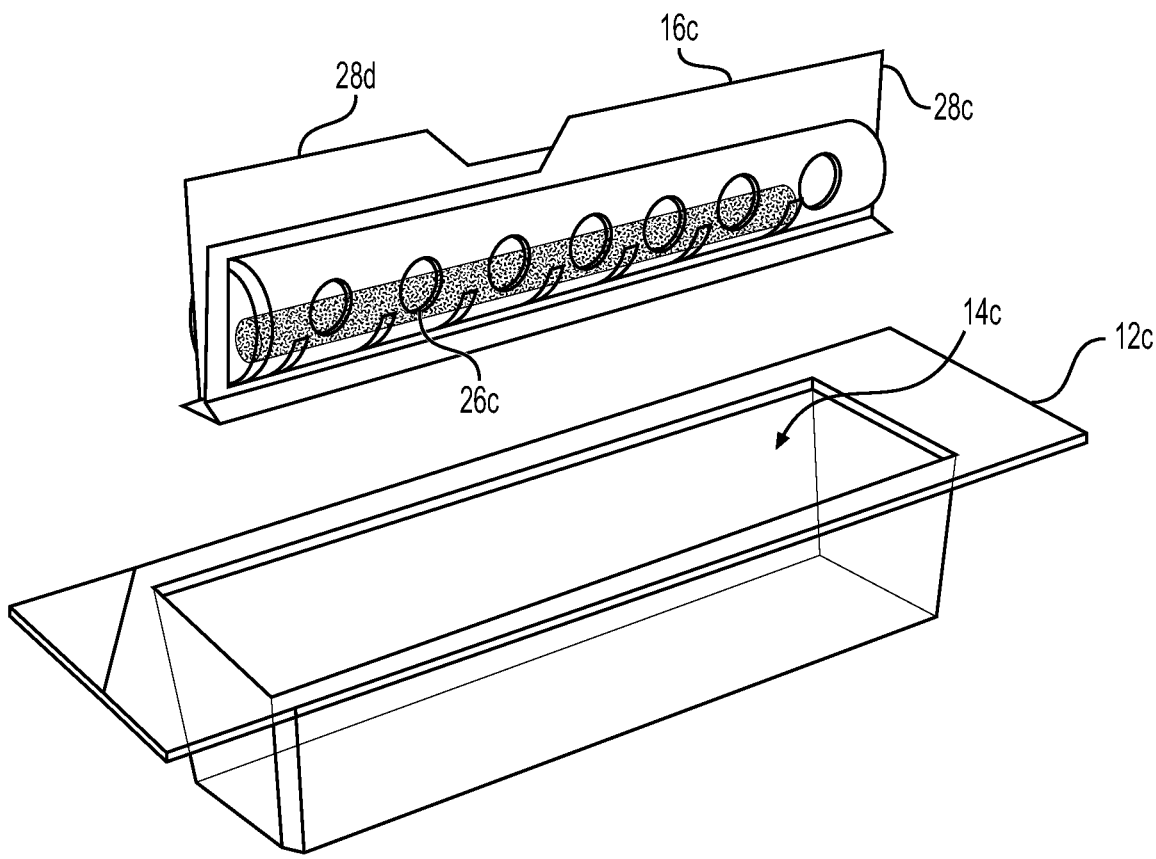
FIG. 3A is an exploded view of a third example embodiment of a packaging system consistent with the present disclosure.
Figure 3B:
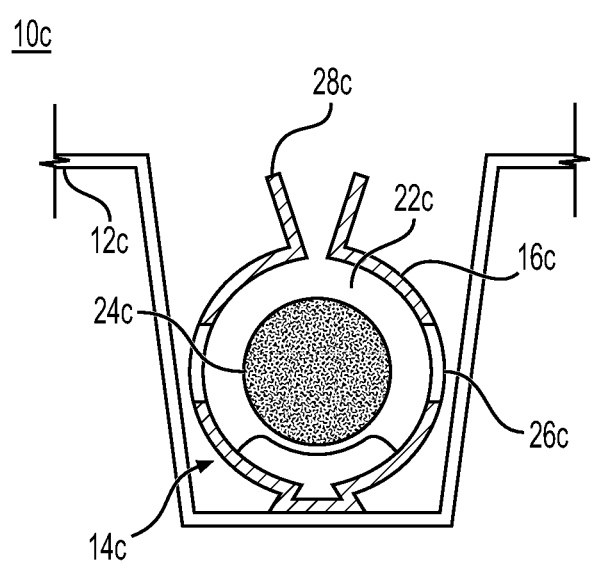
FIG. 3B is a cross-sectional view of the example embodiment of the packaging system of FIG. 3A consistent with the present disclosure.

The packaging body and the cavity defined therein may have any suitable shape and configuration. In an example embodiment, the cavity 14a may have a generally rounded, or semi-cylindrical, shape as shown in FIGS. 1A and 1B. In some such embodiments, the packaging body 12a may be provided with features, such as feet 20a, 20b, that may stabilize the packaging body 12a with the opening of the cavity 14a generally oriented upwardly (e.g., when the packaging body 12a is placed on a generally horizontal surface). In other example embodiments, e.g., as shown in FIGS. 2A and 3A-3B, the packaging body 12b, 12c may be formed having a generally flat bottom, e.g., which may allow the packaging body 12b, 12c to reside in a generally stable orientation with the opening of the cavity 14b, 14c generally oriented upwardly when the packaging body 12b, 12c is placed on a generally horizontal surface. It will be appreciated that shapes and configurations other than the depicted embodiments may be utilized.

As generally discussed, the packaging system may include a tissue cradle that is configured to be at least partially disposed within the cavity. In some embodiments, the tissue cradle may be configured to be removably disposed within the cavity. Further, the tissue cradle may be sized relative to the cavity such that the seal may have a generally planar configuration and may be joined to the packaging body without interference from the tissue cradle. In other embodiments, the seal may have a contoured configuration to accommodate a tissue cradle that at least partially protrudes from the cavity.

In general, the tissue cradle may be configured to support a tissue specimen. That is, the tissue cradle may generally be shaped to retain or position the tissue specimen relative to the tissue cradle. Accordingly, in an implementation in which the tissue cradle may be removably disposed in the cavity of the packaging body, the tissue specimen may be placed within and/or removed from the packaging by placing the tissue cradle (supporting the tissue specimen) within the cavity and/or removing the tissue cradle (supporting the tissue specimen) from the cavity. For example, and referring to FIGS. 1A-2B, in some embodiments, the tissue cradle 16a, 16b may generally be formed as an open tray having an recess, indentation, or cavity (e.g., recess 22a, 22b) that may support the tissue specimen (e.g., by placing the tissue specimen 24a in the recess 22a of tissue cradle 16a as shown in FIG. 1A). In some implementations, the tissue cradle may at least partially surround the tissue specimen. For example, as shown in the embodiment of FIG. 3B, the tissue cradle 16c may have a generally clamshell configuration in which two or more cooperating portions of the tissue cradle 16c may be respectively folded around the tissue specimen 24c to at least partially enclose the tissue specimen 24c. It will be appreciated that a tissue cradle consistent with the present disclosure may have various additional and/or alternative configuration that may support a tissue specimen to allow the tissue specimen to the removably placed within the cavity of the packaging system by removably placing the tissue cradle within the cavity.

In addition and/or as an alternative to allowing the tissue specimen to be removably placed within the cavity, the tissue cradle may also help to protect and/or retain the tissue specimen within packaging system. For example, the tissue cradle may allow a tissue specimen having a relatively small size, by comparison to the cavity of the packaging body, to be relatively positionally retained within the cavity. For example, the tissue cradle may reduce the degree of available movement of the tissue specimen within the cavity (e.g., reduce the degree of sloshing around or lateral movement within the cavity experienced by the tissue specimen). Because the tissue cradle may support a relatively small tissue specimen within a relatively larger cavity, in some embodiments a packaging body may be sized to facilitate manipulation of the packaging system by a user, for example, without requiring a high degree of dexterity. Consistent with the present disclosure, the packaging system may be used for containing any desired tissue. For example, the tissue specimen may include human tissue or animal tissue. Examples of tissues that may be used in connection with the present disclose may include, but are not limited to nerve tissue, vascular tissue, urological tissue, tendons, muscle tissue, etc.

Consistent with some embodiments, the tissue cradle may be configured to at least partially immerse the tissue specimen in a liquid disposed in the cavity. For example, during packaging, the cavity of the packaging body may be at least partially filled with a liquid medium (e.g., either before or after the tissue cradle and/or the tissue specimen are placed within the cavity). The liquid medium may include any suitable liquid, e.g., which may maintain and/or preserve one or more characteristics of the tissue specimen (e.g., to increase storage life, increase bioactivity, increase recipient acceptance, etc.) and/or which may facilitate handling of the tissue specimen, e.g., during removal of the tissue specimen from the cavity and/or during handling of the tissue specimen in a surgical procedure.

According to one example, the liquid may facilitate the storage and/or preservation of the tissue specimen. According to another example, the liquid may include a solution including between about 2% to about 15% by volume dimethyl sulfoxide (DMSO). The solution may also include between about 150 g/L and 2.5 g/L sodium chloride. The solution may also include about 0.3 g/L potassium chloride. The solution may also include about 0.2 g/L calcium chloride. The solution may also include about 0.4 g/L sodium bicarbonate. The solution may further include about 0.1 g/L magnesium chloride. It will be appreciated that various other liquids, including but not limited to, solutions comprising mixtures of monovalent and divalent metal cations (e.g., sodium, potassium, magnesium, calcium, etc.) may be utilized in connection with embodiments consistent with the present disclosure, including the preservation solutions disclosed in U.S. patent application Ser. No. 16/898,224, entitled "Wet Preservation of Tissue," published as US 2020/0390087 A1, and U.S. patent application Ser. No. 16/939,889, also entitled "Wet Preservation of Tissue," published as US 2020/0390088 A1, both of which are incorporated by reference herein.

Figure 2B:
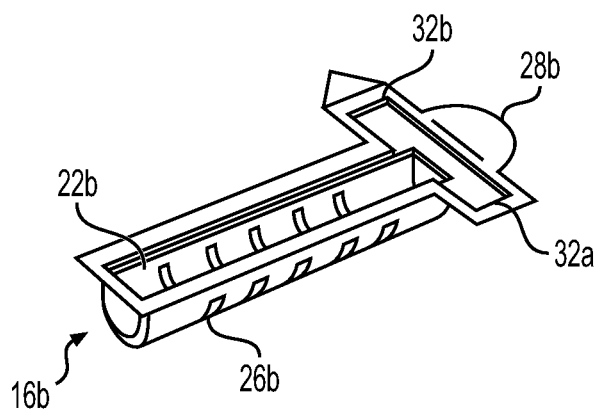
FIG. 2B depicts an example embodiment of a tissue cradle of the illustrative example embodiment of the packaging system of FIG. 2A.

In some embodiments, the tissue cradle may be configured to allow the liquid to drain from the tissue cradle upon removal from the cavity. For example, as discussed above, the tissue cradle may be configured to at least partially immerse the tissue specimen in a liquid when the tissue cradle is at least partially disposed within the cavity. Further, the tissue cradle may be configured to allow the liquid to drain from the tissue cradle (and thereby drain from around the tissue specimen) when the tissue cradle is removed from the cavity. For example, the tissue cradle may include any variety of slots, holes, cutouts, perforations, of the like that may allow the liquid to drain from the recess or interior of the tissue cradle the supports the tissue specimen. Referring to FIGS. 1B and 2B, in the illustrated embodiments the tissue cradles 16a and 16b may include one or more slots (e.g., slots 26a, 26b) in the recesses 22a, 22b or the respective tissue cradles 16a, 16b. The slots 26a, 26b may allow liquid to drain from the tissue cradles 16a, 16b while still allowing the tissue cradles 16a, 16b to continue to support the tissue specimen. In the further illustrated example of FIG. 3A-3B, the clamshell tissue cradle 16c may include a plurality of holes (e.g., holes 26c) that may allow liquid to drain from the interior of the clamshell tissue cradle 16c, while allowing the clamshell tissue cradle 16 to continue to support the tissue specimen 24c. It will be appreciated that various additional and/or alternative configurations may be provided to allow liquid to drain from the tissue cradle which allowing to the tissue cradle to continue supporting the tissue specimen, e.g., upon removal of the tissue cradle from the cavity.

In some embodiments consistent with the present disclosure, the tissue cradle may include one or more features configured to facilitate manipulation of the tissue cradle. For example, as generally discussed above, the tissue cradle may support a tissue specimen within the cavity. Removal of the tissue specimen from the packaging system may be facilitated by removal of the tissue cradle from the cavity. For example, the tissue cradle may generally be of a larger size and greater structural integrity (e.g., strength, stiffness, etc.) than the tissue specimen. As such, it may be easier to remove the tissue cradle, still supporting the tissue specimen, from the cavity than to remove the tissue specimen from the tissue cradle while it is still in the cavity. Additionally, as discussed above, the tissue cradle may include features, such as holes, slots, etc., which may allow the liquid to drain from the tissue cradle, and thereby drain from around the tissue specimen, when the tissue cradle is removed from the cavity. To this end, the tissue cradle may include one or more features that may facilitate manipulation of the tissue cradle, e.g., manually and/or by surgical instruments such as forceps or tweezers.

Consistent with the foregoing, in various embodiments, the tissue cradle may include features, such as extensions, tabs, flaps, additional material around the perimeter, as well as other suitable features that may facilitate handling and manipulation of the tissue cradle. Referring to FIGS. 1A-1B, in an example embodiment, the tissue cradle 16a may include an extension 28a from one end of the recess 22a. The extension 28a may provide a convenient feature that can more easily be grasped by tweezers or forceps, e.g., to remove the tissue cradle 16a from the cavity 14a. Similarly, in the embodiment of FIGS. 2A-2B, the tissue cradle 16b is shown including extension 28b from the recess 22b. Consistent with this embodiment, the extension 28b may not only extend longitudinally relative to the recess 22b, but may also include laterally extending features as well. Further, referring to FIGS. 3A and 3B, the features 28c, 28d may include tabs of the opposed sides of the clamshell tissue cradle 16c, e.g., which may allow the tissue cradle to be more easily grasped and manipulated. Further, as shown, in some embodiments the features 28c and 28d may be at least partially offset from one another, e.g., which may facilitate opening the clamshell tissue cradle 16c, for example to extract the tissue specimen 24c from the tissue cradle 16c.

As generally discussed above, the tissue cradle may be configured to allow liquid to drain from the tissue cradle. In some implementations, it may be desirable to rinse the tissue specimen prior to use (e.g., prior to implanting the tissue specimen in a recipient). Methods of and the liquids and solutions used in rinsing the stored tissue in preparation for its use, e.g., in a patient in a surgical setting, may be dependent on the storage solution used and type of tissue preserved. Such methods and rinse liquids, and variations thereon, will be appreciated by those of skill in the art. For example, the methods and rinse liquids disclosed in U.S. patent application Ser. No. 16/898,224, entitled "Wet Preservation of Tissue," published as US 2020/0390087 A1, and U.S. patent application Ser. No. 16/939,889, also entitled "Wet Preservation of Tissue," published as US 2020/0390088 A1, both of which are incorporated by reference herein, may be used. Consistent with such an embodiment, not only may the manipulation features (e.g., features 28a-d) facilitate removal of the tissue cradle from the cavity, but the manipulation features may also facilitate rinsing of the tissue specimen, e.g., by providing a convenient portion of the tissue cradle to grasp for lowering the tissue cradle into a rinse basin and/or swishing the tissue cradle (and the tissue specimen supported by the tissue cradle) in a basin containing a rinse liquid. In this regard, the drainage features of the tissue cradle may also facilitate rinsing of the tissue specimen, e.g., by similarly allowing the rinse liquid to drain from the tissue cradle.

According to some embodiments consistent with the present disclosure, the cavity of the packaging system may be configured to at least partially receive tissue cradles of different sizes. For example, in some situations it may be desirable to provide the tissue cradle having a recess that is sized to accommodate a tissue specimen of a given size. For example, it may be desirable that the recess of the tissue cradle be a similar size as the tissue specimen, e.g., to allow less movement of the tissue specimen within the recess, etc. Accordingly, a tissue cradle with a relatively larger recess may be utilized for supporting a relatively larger tissue specimen, and a tissue cradle with a relatively smaller recess may be utilized for supporting a relatively smaller tissue specimen. Consistent with some such arrangements, it may be desirable to be able to use the same packaging body, having the same sized cavity, with tissue cradles having different sized recesses. Further, it may be desirable that regardless of the size of the recess of the tissue cradle, that the freedom of movement of the tissue cradle within the cavity be limited (e.g., to prevent the tissue specimen from being dislodged from the recess, or otherwise moved in a manner that the tissue cradle no longer supports the tissue specimen).

Consistent with the foregoing, in an embodiment in which the cavity may be configured to at least partially receive cradles of different sizes, the overall size of the cradle may be independent of the size of the recess for supporting the tissue specimen. For example, in the illustrated embodiment of FIGS. 1A-1B, the tissue cradle 16a may include the recess 22a and the extension 28a. The overall size of the tissue cradle 16a may be generally similar and/or have a generally similar cross-sectional and/or plan-view size and/or shape as the cavity 14a. As such, the tissue cradle 16a may be generally positionally constrained within the cavity 14a. In an example embodiment, the cavity 14a may be configured to at least partially receive different tissue cradles have a similar overall size, but having differently sized recesses. For example, a tissue cradle having a relatively larger recess (e.g., which may be configured to support a relatively larger tissue specimen) may have a relatively smaller extension, and thereby have a generally similar overall size. Similarly, a tissue cradle having a relatively smaller recess (e.g., which may be configured to support a relatively smaller tissue specimen) may have a relatively larger extension. It will be appreciated that in addition to having varyingly sized longitudinal extensions, tissue cradles having differently sized recesses may also have varyingly sized lateral extensions, e.g., to provide a generally similar overall size and/or shape.

In some embodiments, a cavity having a single size may be configured to accommodate differently sized tissue cradles while generally positionally constraining the tissue cradle relative to the cavity. For example, as discussed above, different tissue cradles may be provided having different sized recesses for supporting different sized tissue specimens. In the example discussed relative to FIGS. 1A and 1B, the different tissue cradles having different size recesses may be positionally constrained relative to the cavity by providing the different tissue cradles with a similar overall size (e.g., even though the recesses may be different sizes). Consistent with another example, the cavity and the tissue cradle may include features that may positionally constrain the tissue cradle relative to the cavity. For example, as shown in FIG. 2A, the cavity 14b may include at least one slot (e.g., slots 30a-30d) configured to engage a corresponding tab (e.g., tabs 32a-32b) of the tissue cradle 16b for maintaining a position of the tissue cradle 16b within the cavity 14b.

Consistent with the foregoing, in some embodiments the cavity and each of the plurality of tissue cradles may include cooperating features to support any of the plurality of tissue cradles within the cavity. For example, the extension 28a of the tissue cradle 16a may be configured to cooperate with the overall dimensions of the cavity 14a. Further, the tabs 32a, 32b may be configured to cooperate with the slots 30a-30d of cavity 14b. As such, a plurality of cradles configured to support differently sized tissue specimens may be utilized with a commonly sized and/or configured cavity.

It will be appreciated that while the illustrated embodiment utilizes four slots 30a-30d on either side of the cavity 14b, a greater or fewer number of slots may be utilized. Additionally, while the embodiment in FIGS. 2A and 2B includes slots on each side of the cavity, and tabs on each side of the tissue cradle, in other embodiments slots may be provided only on one side of the cavity, and a tab may be provided only on one side of the tissue cradle. It will also be appreciated that cooperating features other than slots and tabs may be utilized to achieve the same result.

In another example, in addition to positionally constraining the tissue cradle relative to the cavity, the cooperating features may provide an indication of a size of the tissue specimen supported by the tissue cradle. For example, as shown in FIG. 2A, each of the slots 30a-30d include an associated size marking. Consistent with such an example the size marking may correspond to a size of a tissue specimen that may be retained by a tissue cradle that may engage the slot associated with the size marking. Accordingly, the cooperating features may also provide a size indicator for the tissue specimen.

Consistent with the foregoing, in some embodiments, the tissue cradle may include one of a plurality of tissue cradles. Each of the plurality of tissue cradles may be differently-sized, that is, configured to support differently-sized tissue specimens (e.g., each of the plurality of tissue cradles may include a differently-sized recess). In some such embodiments, the tissue cradles sized to support tissue specimens of different sizes may be used with a packaging cavity of the same size. However, in other embodiments, tissue cradles configured to support tissue specimens of different sizes may themselves be of a different size, but may be configured to be used in a packaging cavity of the same size (e.g., one cavity size may accommodate different sizes of tissue cradles) and may include cooperating features between the tissue cradles and the cavity for positionally constraining the tissue cradle relative to the cavity.

In some examples, the tissue cradle may be configured to support tissue specimens having a plurality of sizes. For example, and referring to FIG. 1A, in one embodiment, the tissue cradle 16a may include recess 22a that is sized to support tissue specimens of a given length (e.g., 15 mm in the illustrated example). Further, the recess 22a may be sized to support tissue specimens of the given length, but having different diameters (e.g., tissue specimens 24d, collectively). For example, the width and depth of the recess 22a may be sized for supporting a largest diameter tissue specimen of the given length, and may also suitably support tissue specimens of the given length of a smaller diameter than the largest diameter tissue specimen. It will be appreciated that while the recess 22a may be sized to support a tissue specimen of a given length, that the recess 22a can similarly support tissue specimens having a shorter length.

With reference also to FIGS. 3A-3B, in some example embodiments a single sized tissue cradle 16c may be configured for supporting tissue specimens of different lengths and/or different diameters. For example, tissue cradle 16c may have a clamshell configuration, e.g., which may be closed around the tissue specimen to both support the tissue specimen and retain the tissue specimen in the enclosed recess defined by the clamshell. As such, the enclosed recess may support larger and smaller tissue specimens while resisting the tissue specimen from becoming dislodged from the tissue cradle 16c (e.g., as a tissue specimen disposed within the clamshell tissue cradle may be encompassed on all sides by the tissue cradle).

As generally discussed above, the packaging system may include a seal configured to be joined to the packaging body to fluidly seal the cavity. As shown in the various illustrated embodiments, the cavity of each packaging system may generally include an open surface. The seal may be joined to the packaging body around the perimeter of the cavity to fluidly seal the cavity, and to retain the tissue cradle and tissue specimen within the cavity. Further, the seal may not only prevent the escape of the any storage liquid that may be utilized in connection with the tissue specimen, but the seal may also prevent the ingress of any contaminants, e.g., which may adversely affect the tissue specimen and/or compromise the intended use of the tissue specimen. In some implementations, the seal may additionally provide an oxygen barrier, e.g., to prevent and/or reduce the intrusion of oxygen into the cavity once the seal has been joined to the packaging body.

It will be appreciated that a variety of suitable materials may be used for the seal. Examples of such materials may include, but are not limited to, a plastic film, a metal foil, a multilayer structure (e.g., a plastic laminated paper, a plastic laminated metal foil, a multi-layer plastic film, etc.). Additionally, it will be appreciated that a variety of techniques may be utilized for joining the seal to the packaging body to provide a fluid-tight seal. For example, the seal may be adhesively bonded to the packaging body, may be head bonded to the packaging body, and/or otherwise joined to the packaging body. Further, it will be appreciated that, while the illustrated embodiments have generally depicted the seal as a planar member, in other embodiments, the seal may include a shape and/or contoured member. In some such embodiments, the seal may include an additional cavity that may be at least partially aligned with the cavity of the packaging body when the seal is joined to the packaging body.

In an example embodiment, the seal may be configured to be peeled from the packaging body to allow access to the cavity (e.g., to allow removal of the tissue cradle and/or the tissue specimen from the cavity). For example, as discussed above, the seal may be joined to the packaging body, e.g., by adhesive bonding and/or heat bonding (e.g., heat sealing). In some embodiments, a portion of the seal may be not be joined to the packaging body. For example, a portion of the seal may extend peripherally beyond the joint between the seal and the packaging body. For example, as shown in FIGS. 1A and 2A, the seal 18a, 18b (respectively) may include a flap portion 34a, 34b (respectively). When the seal 18a, 18b is joined to the packaging body, at least the flap portion 34a, 34b may not be joined to the packaging body 12a, 12b and may extend beyond the joint between the seal 18a, 18b and the packaging body 12a, 12b. The flap portions 34a, 34b may provide a convenient location for grasping the seal 18a, 18b for peeling the seal 18a, 18b from the packaging body 12a, 12b. Similarly, the packaging body 12a, 12b may include a tab 36a, 36b (respectively) that may extend peripherally beyond the joint between the seal 18a, 18b, and the packaging body 12a, 12b. In a similar manner as flap portions 34a, 34b, the tab portions 36a, 36b may provide a portion of the packaging body 12a, 12b for grasping the packaging body 12a, 12b for peeling the seal 18a, 18b from the packaging body 12a, 12b. Consistent with various other embodiments, the seal may be cut or torn away from the packaging body to allow access to the cavity (e.g., to remove the tissue cradle and/or the tissue specimen).

Figure 4A:
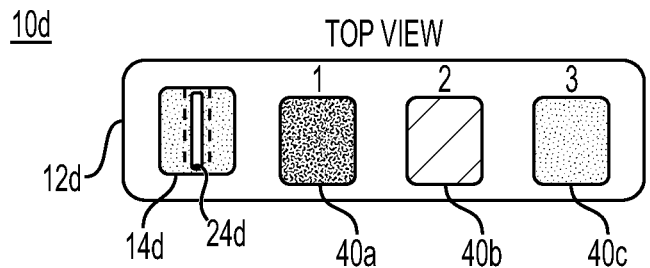
FIG. 4A is a top view of another example embodiment of a packaging system consistent with the present disclosure.
Figure 4B:
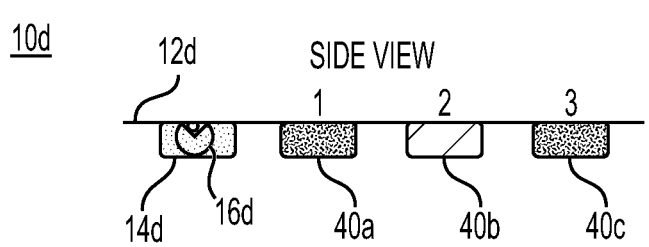
FIG. 4B is a side view of the example embodiment of a packaging system of FIG. 4A consistent with the present disclosure.
Figure 5A:
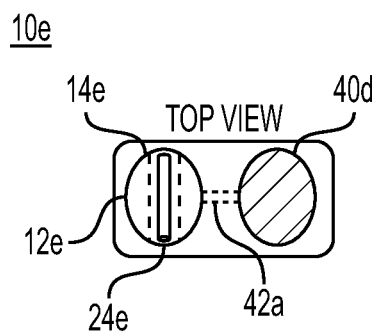
FIG. 5A is a top view of another example embodiment of a packaging system consistent with the present disclosure.
Figure 5B:
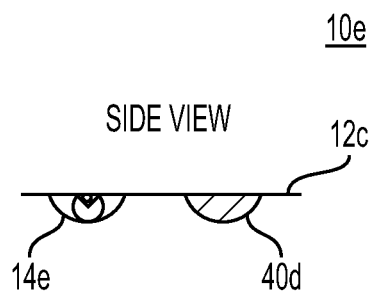
FIG. 5B is a side view of the example embodiment of a packaging system of FIG. 5A consistent with the present disclosure.

Referring to FIGS. 4 through 6, according to another example, a packaging arrangement may be provided that may include one or more reservoirs for containing one or more rinse or wash solutions. For example, referring to the example of FIGS. 4A and 4B, an example packaging system 10d. As shown, the packaging system 10d may include a packaging body 12d that may define a cavity 14d for containing a tissue specimen 24d. In some embodiments, the tissue specimen 24d may be supported by a tissue cradle 16d, while in other embodiments, the tissue specimen may be supported by the cavity itself. Consistent with various implementations, the cavity 14d and/or the tissue cradle 16d may be configured in a manner similar with any previously described cavities and/or tissue cradles, and/or including various combinations of features of the previously described cavities and tissue cradles. In other implementations, the cavity 14d and/or tissue cradle 16d may have different features and/or configurations than previously described embodiments. Further, as generally mentioned, in some embodiments, the packaging system 10d may not include a tissue cradle. Consistent with such an embodiment, the tissue specimen 24d may be supported by the cavity 14d.

In addition to the cavity 14d, the packaging system 10d may include one or more additional reservoirs 40a-40c. The one or more additional reservoirs 40a-40c may include cavities formed in the packaging body 12d, which may be configured for holding a volume of liquid. As discussed with preceding embodiments, the packaging system 10d may include a seal (not shown), which may enclose the one or more reservoirs 40a-40c (in a sealed configuration), and may be peeled from the packaging body 12d to allow access to the one or more reservoirs 40a-40c. In some implementations, the seal may be incrementally peeled from the packaging body 12d to incrementally allow access to the cavity 14d and the one or more reservoirs 40a-40d. For example, the seal may be peeled from the packaging body 12d to allow access to the cavity 14d. Subsequently, the seal may be peeled from the packaging body 12d to allow access to the first reservoir 40a. Then, the seal may be peeled from the packaging body 12d to allow access to the second reservoir 40b. Further, the seal may be peeled from the packaging body 12d to allow access to the third reservoir 40c. It will be appreciated that other configurations may also be implemented, e.g., peeling the seal from the packaging body to expose more than one reservoir at a time, etc.

In some implementations, the one or more reservoirs may be utilized for containing liquids and/or articles that may be used in connection with the preparation, use, and/or implantation of the tissue specimen. For example, in some implementations, the tissue specimen may be preserved using a preservation medium, such as a preservation solution or treatment. In some such implementations, it may be desirable to rinse or wash the tissue specimen prior to use (e.g., prior to implantation or other use) to at least partially remove or displace the preservation medium. In such an embodiment, one or more of the reservoirs may contain a rinse or wash liquid. According to an example, during use of the tissue specimen 24d, the tissue specimen 24d may be removed from the cavity 14d and may be exposed to a rinse or wash liquid contained in one or more of the reservoirs 40a-40c, e.g., by placing the tissue specimen 24d in one or more of the reservoirs 40a-40c and/or by submerging and/or swishing the tissue specimen 24d in a liquid contained in one or more of the reservoirs 40a-40c. In one embodiment, the tissue specimen 24 may be sequentially exposed to a liquid contained in each respective reservoir 40a-40c. In some implementations, each reservoir 40a-40c may contain the same liquid. In some implementations, one or more of the reservoirs 40a-40c may include a different liquid than one or more of the other reservoirs 40a-40c. For example, different liquids may be contained in different reservoirs to allow sequential washing, rinsing, and/or treatment of the tissue specimen. Examples of rinse and/or wash liquids may include, but are not limited to, water, saline solution, Lactated Ringers Solution ("LRS"), phosphate buffered saline ("PBS"), or other suitable rinse solution/liquid. In addition and/or as an alternative to a liquid, one or more of the reservoirs may include a piece of apparatus or other article that may be associated with the use of the tissue specimen. As such, the packaging system 10d may provide and protect both the tissue specimen and the associated apparatus or article. Other implementations may also be utilized. It will be appreciated that while three reservoirs are depicted, this is for illustrative purposes only, as a greater or lesser number of reservoirs may be provided.

Referring to FIGS. 5A-5B and 6A-6B, according to further examples, the one or more reservoirs may be capable of being fluidly coupled with the cavity. For example, the one or more reservoirs may be capable of being fluidly coupled with the cavity while the seal remains coupled to and/or joined to at least a portion of the packaging body. For example, and referring to FIGS. 5A and 5B, an example of a packaging system 10e is shown including a cavity 14e and a reservoir 40d. As shown, the cavity 14e may be configured to retain a tissue specimen, either with or without the use of a tissue cradle. Consistent with the embodiment, the packaging system 10e may include a fluid pathway 42a between the cavity 14e and the reservoir 40d. For example, the seal (not shown) may be joined to the packaging body 12e in a manner such that the seal is more weakly joined to the packaging body 12e in the region of the fluid pathway 42a than to the surrounding portions of the packaging body 12e. Consistent with such an embodiment, the application of pressure to either the cavity 14e or the reservoir 40d may cause an increase in pressure in either the cavity 14e and/or the reservoir 40d. The increase in pressure may cause the joint between the seal and the packaging body 12e to fail along the fluid pathway 42a. The failure of the joint between the seal and the packaging body 12e along the fluid pathway may allow fluid communication between the cavity 14e and the reservoir 40d.

In one example, pressure may be applied to the reservoir 40d, e.g., as by squeezing the packaging system 10e in the region of the reservoir 40d. The applied pressure may cause an increase in the pressure of a rinse solution, and/or other fluid, within the reservoir 40d, which may result in a failure of the bond between the seal and the packaging body 12e in the region of the fluid pathway 42a. The failure of the bond between the seal and the packaging body in the region of the fluid pathway may allow fluid communication between the reservoir 40d and the cavity 14e via the fluid pathway 42a. In some embodiments, once the fluid pathway 42 has been opened up (e.g., by failure of the bond between the seal and the packaging body 12e), the increased pressure within the reservoir 40d may allow an at least partial transfer of fluid from the reservoir 40d into the cavity 14e. In some implementations, the at least partial transfer of fluid from the reservoir into the cavity may initiate rinsing and/or washing of the tissue specimen. It will be appreciated that the fluid pathway 42a may represent a line and/or region of relatively weak bonding between the seal and the packaging body. In some embodiments, the seal may be un-bonded to the packaging body in the region of the fluid pathway. Further, a relatively thin line of bonding between the seal and the packaging body may be provided across the fluid pathway (e.g., at one or more regions between a junction of the fluid pathway and a junction of the fluid pathway and the reservoir). In such an embodiment, rather than cause a failure of the joint between the seal and the packaging body along the entirety of the fluid pathway, the increase in pressure may only cause a failure of a relatively smaller expanse of the joint between the seal and the packaging body along the fluid pathway, and thus provide the fluid pathway for fluid communication between the cavity and the reservoir. Consistent with any of the foregoing arrangements, the reservoir may be fluidly isolated from the cavity until the fluid pathway is opened up through the failure of the joint between the seal and the packaging body.

Figure 6A:
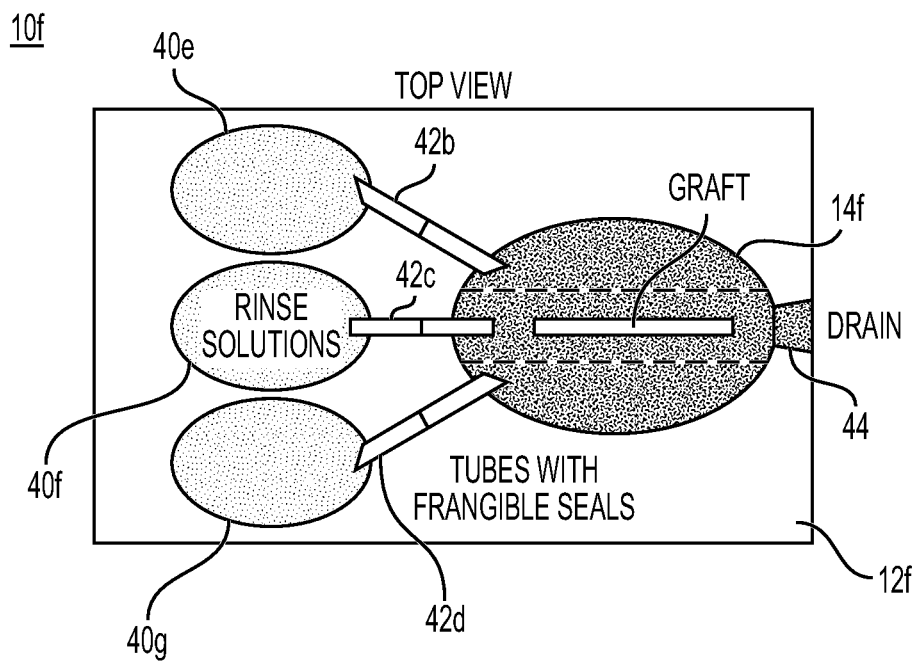
FIG. 6A is a top view of another example embodiment of a packaging system consistent with the present disclosure.
Figure 6B:
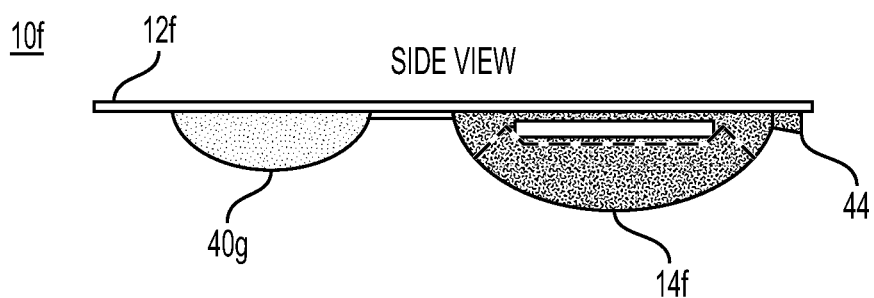
FIG. 6B is a side view of the example embodiment of a packaging system of FIG. 6A consistent with the present disclosure.

Referring also to FIGS. 6A and 6B, in some embodiments, a packing system 10f may include more than one reservoir (e.g., reservoirs 40e-40g) that may be capable of being in fluid communication with a cavity 14f via one or more respective fluid pathways (e.g., fluid pathways 42b-42d). For example, the cavity 14f and reservoirs 40e-40g may be formed in a packaging body 12f, in a manner as generally discussed above with respect to one or more of the preceding example embodiments. The cavity 14f may be configured to retain a tissue specimen, with and/or without the use of a tissue cradle. The one or more reservoirs 40e-40g may include one or more fluids (e.g., which may include the same fluid in each reservoir and/or one or more different fluids) that may be at least partially transferred to the cavity 14f via one or more fluid pathways 42b-42d. Accordingly, it may be possible expose the tissue specimen to more than one different fluid and/or to provide sequential exposure to fluids (e.g., to provide sequential rinsing, etc.).

In some embodiments, one or more of the fluid pathways may include regions in which the seal (not shown) is more weakly joined to the packaging body 12f as compared to surrounding regions. As such, a pressure applied to a fluid within one or more of the reservoirs 40e-40g may cause a localized failure of the bond along the respective fluid pathway. In other embodiments, the fluid pathways may represent regions along with the seal is not joined to the packaging body 12f, except for, for example, at discrete regions between the junction of the fluid pathway and the reservoir and the junction between the fluid pathway and the cavity. Such discrete regions may represent frangible seals. The frangible seals may maintain fluid isolation between the cavity 14f and the respective reservoirs 40e-40g, until such time that one or more of the frangible seals are ruptures (e.g., by applying force to one or more respective reservoirs). In some embodiments, one or more of the fluid pathways 42b-42d may include channels formed in the packaging body and/or in the seal. Consistent with such an embodiment, the fluid pathways may include discrete frangible seals, e.g., which may fluidly isolate the respective reservoirs and the cavity until the respective frangible seals are ruptured (e.g., through the application of pressure to one or more respective reservoirs). The frangible seals may include any material that may fluidly seal the fluid pathways, but which may burst or rupture through the application of pressure to respective reservoirs. In some embodiments, the frangible seals may rupture at a lower applied pressure to the reservoirs than a pressure that may cause failure of the joint between the seal and the packaging body. As such, the frangible seals may be ruptured, to provide fluid communication between one or more reservoirs and the cavity without otherwise compromising the packaging system. While a separate fluid pathway is depicted between each reservoir and the cavity, it will be appreciated that in some embodiments, at least a portion of the fluid pathways may be common. For example, each reservoir may be coupled with a common fluid pathway to the cavity by way of one or more feeder pathways, and/or directly via respective frangible seals.

In some embodiments, the cavity may include a drain, e.g., which may provide fluid communication with an exterior of the packaging system. For example, as shown in the illustrated example of FIGS. 6A and 6B, the cavity 14f may include a drain 44, which may provide fluid communication with an exterior of the packaging system 10f. In some embodiments, the drain 44 may include a frangible seal consistent with any of the previously described frangible seals (e.g., as a region of relatively weak bonding between the seal and the packaging body 12f, a frangible member disposed within the drain, or the like). As discussed above, in some embodiments, pressure may be applied to a reservoir, e.g., which may open a fluid pathway between the reservoir and the cavity (e.g., by rupturing a frangible seal and/or causing a bond failure between the seal and the packaging body, etc.). Additionally, the increased pressure on the reservoir may cause an increase in the pressure within the cavity once the fluid pathway between the reservoir and the cavity has been opened. In some embodiments, this resulting increase in pressure within the cavity may cause the drain 44 to open (e.g., by rupturing a frangible seal and/or cause a bond failure between the seal and the packaging body). As such, the cavity may be in fluid communication with the exterior of the packaging system. This may allow at least a portion of the fluid within one or more reservoirs to be transferred to the cavity, e.g., by providing a drain for any fluid already within the cavity (and/or previously transferred to the cavity from a reservoir) to exit the cavity. Accordingly, in some such embodiments, it may be possible to flush fluid from the cavity, for example, by displacing it with fluid from one or more of the reservoirs. Further, this approach may be utilized to sequentially rinse and/or treat the tissue specimen with liquids from the reservoirs.

While some of the foregoing example embodiments have been described in the context of packaging systems for tissue specimens, it will be appreciated that the principles, features, and/or advantages described herein may be equally applicable to packaging for other materials. Additionally, while some of the foregoing example embodiments have been described in the context of packaging systems for tissue specimens stored in a liquid medium, it will be appreciated that the principles, features and/or advantages described herein may be equally applicable to storing tissue without the use of a liquid medium. Accordingly, the present disclosure should not be limited by any of the disclosed example embodiments, and should be afforded the full scope of the appended claims.

What is claimed is:

1. A packaging system comprising:
   (a) a packaging body defining a cavity;
   (b) a plurality of tissue cradles each configured to be disposed within the cavity; and
   (c) a seal configured to be joined to the packaging body to fluidly seal the cavity,
   wherein the plurality of tissue cradles are of different sizes.

2. The packaging system according to claim 1, wherein the cavity is configured to receive tissue cradles of different sizes.

3. The packaging system according to claim 1, wherein the cavity comprises at least one slot configured to engage a corresponding tab of the tissue cradle for maintaining a position of the tissue cradle within the cavity.

4. The packaging system according to claim 1, wherein the tissue cradle is configured to support a tissue specimen and to fit within the cavity to at least partially immerse the tissue specimen in a liquid disposed in the cavity.

5. The packaging system according to claim 4, wherein the tissue cradle includes one or more openings to allow the liquid to drain from the tissue cradle upon removal from the cavity.

6. The packaging system according to claim 1, wherein the tissue cradle includes one or more features configured to facilitate manipulation of the tissue cradle.

7. The packaging system according to claim 1, wherein the packaging system comprises a plurality of tissue cradles, and wherein the plurality of tissue cradles are configured to support tissue specimens having a plurality of sizes.

8. The packaging system according to claim 1, wherein the packaging system comprises a plurality of tissue cradles, and wherein the plurality of tissue cradles are a plurality of different sizes, and wherein the cavity and each of the plurality of tissue cradles include cooperating features to support any of the plurality of tissue cradles within the cavity.

9. The packaging system according to claim 1, wherein the seal includes a plastic film or a foil.

10. The packaging system according to claim 1, wherein the seal is configured to be peelable from the packaging body to allow access to the cavity.

11. A packaged plurality of tissue specimens, wherein the tissue specimens are packaged in a tissue packaging system comprising:
    (a) a packaging body defining a cavity;
    (b) a plurality of tissue cradles disposed within the cavity; and
    (c) a seal joined to the packaging body to fluidly seal the cavity, wherein the tissue specimens are supported by the tissue cradles, and wherein the plurality of tissue cradles are of different sizes.

12. The packaged tissue specimen according to claim 11, wherein the tissue specimen includes one or more of:
    nerve tissue, vascular tissue, urological tissue, tendons, or muscle tissue.

13. The packaged tissue specimen according to claim 11, wherein the tissue cradle of the tissue packaging system is configured to at least partially immerse the tissue specimen in a liquid disposed in the cavity, and wherein the tissue cradle of the tissue packaging system includes one or more openings to allow the liquid to drain from the tissue cradle upon removal from the cavity.

14. The packaged tissue specimen according to claim 11, wherein the tissue cradle of the tissue packaging system includes one or more features configured to facilitate manipulation of the tissue cradle, and wherein the tissue cradle of the tissue packaging system is configured to support the size of the tissue specimen.

15. The packaged tissue specimen according to claim 11, wherein the seal of the tissue packaging system includes a plastic film or a foil seal.

16. The packaged tissue specimen according to claim 15, wherein the seal of the tissue packaging system is peelable from the packaging body to allow access to the cavity.

17. A method of packaging tissue in the packaging system of claim 1, comprising:
    (a) supporting a tissue specimen with a tissue cradle;
    (b) placing the tissue cradle within a cavity defined in a packaging body;

(c) at least partially filling the cavity with a liquid; and
(d) coupling a seal to the packaging body to fluidly seal the cavity.

18. The method according to claim 17, wherein the tissue cradle is selected from a plurality of tissue cradles of different sizes, and wherein the cavity is configured to receive each of the tissue cradles of different sizes.

19. The method according to claim 17, wherein the tissue specimen includes one or more of:
   nerve tissue, vascular tissue, urological tissue, tendons, or muscle tissue.

20. The method according to claim 17, wherein the tissue cradle is configured to at least partially immerse the tissue specimen in the liquid disposed in the cavity.

21. The method according to claim 17, wherein the tissue cradle includes one or more openings to allow the liquid to drain from the tissue cradle upon removal from the cavity.

22. The method according to claim 17, wherein the tissue cradle includes one or more features configured to facilitate manipulation of the tissue cradle.

23. The method according to claim 17, wherein the seal includes one of a plastic seal and a foil seal.

24. The method according to claim 17, wherein coupling the seal to the packaging body includes one of adhesively bonding and heat sealing.

25. The method according to claim 24, wherein the coupled seal is configured to be peeled from the packaging body to allow access to the cavity.

* * * * *